(12) United States Patent
Liang (10) Patent No.: US 6,792,798 B2
(45) Date of Patent: Sep. 21, 2004

(54) ULTRASONIC CYLINDRICAL RESONATOR TO FACILITATE BUBBLE POINT PRESSURE MEASUREMENT

(75) Inventor: Kenneth K. Liang, New Milford, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/167,516

(22) Filed: Jun. 12, 2002

(65) Prior Publication Data

US 2003/0230139 A1 Dec. 18, 2003

(51) Int. Cl.$^7$ .......................... E21B 49/08; E21B 48/10; G01V 1/40
(52) U.S. Cl. ................... 73/152.58; 73/152.18; 73/152.47; 73/152.54; 73/152.55
(58) Field of Search ................... 73/152.18, 152.23, 73/152.24, 152.28, 152.47, 152.54, 152.55, 152.58, 152.27, 863.83, 19.03, 61.47, 61.45, 600, 590, 599; 166/250.01, 309

(56) References Cited

U.S. PATENT DOCUMENTS

| | | | | |
|---|---|---|---|---|
| 2,490,273 A | * | 12/1949 | Kean | 171/330 |
| 4,070,167 A | * | 1/1978 | Barbee et al. | 55/192 |
| 4,092,858 A | * | 6/1978 | Edgerton | 73/170 A |
| 4,369,100 A | * | 1/1983 | Sawyer | 204/157.1 S |
| 4,418,565 A | * | 12/1983 | St. John | 73/19.01 |
| 4,722,224 A | * | 2/1988 | Scheller et al. | 73/599 |
| 4,951,749 A | | 8/1990 | Carroll | 166/264 |
| 5,097,698 A | * | 3/1992 | Wood et al. | 73/54.01 |
| 5,454,255 A | * | 10/1995 | Kraus et al. | 73/19.03 |
| 5,769,608 A | * | 6/1998 | Seale | 417/53.01 |
| 6,058,773 A | | 5/2000 | Zimmerman et al. | 73/152.24 |
| 6,128,949 A | * | 10/2000 | Kleinberg | 73/152.18 |
| 6,223,822 B1 | | 5/2001 | Jones | 166/250.05 |

FOREIGN PATENT DOCUMENTS

| | | | | |
|---|---|---|---|---|
| GB | 2338563 A | * | 12/1999 | E21B/49/08 |
| GB | 2 345 137 B | | 12/1999 | E21B/47/06 |

OTHER PUBLICATIONS

Society of Automotive Engineers, "Dictionary of Aerospace Engineering", 1992, p. 117.*

* cited by examiner

Primary Examiner—Hezron Williams
Assistant Examiner—David A. Rogers
(74) Attorney, Agent, or Firm—Jody Lynn DeStefanis; William B. Batzer; John J. Ryberg (57) ABSTRACT

The present invention discloses an acoustic resonator device capable of nucleating bubbles in a formation fluid under borehole-like conditions wherein the static pressure is higher than the bubble point pressure. The device is comprised of one or more coaxial layers forming a central conduit, wherein at least one of the coaxial layers is comprised of an electro-acoustic transducer material such as including piezoelectric or magnetorestrictive materials. This device is preferably designed to be in fluid communication with a host tool to allow in-situ sampling and bubble point determination. Also disclosed is an in-situ method of fluid analysis in a borehole for determining phase characteristics of a formation fluid using the device. Cavitation may be induced using the device in either a captured volume sample or a flow-line sample.

34 Claims, 8 Drawing Sheets

ULTRASONIC CYLINDRICAL RESONATOR TO FACILITATE BUBBLE POINT PRESSURE MEASUREMENT

FIELD OF THE INVENTION

The present invention relates to an apparatus useful for measuring the bubble point pressures of fluids and a method of using the same and, more particularly, to a multi-layered coaxial piezo-electric resonator for bubble point pressure measurement that is easily integrated with typical borehole fluid sampling tools.

BACKGROUND OF THE INVENTION

A primary objective of borehole formation fluid sampling is to provide accurate determination of the physical and chemical properties of formation fluids. These properties can be strongly affected by temperature and pressure. Therefore, the in-situ temperature and pressure of fluid samples should be maintained throughout the extraction, conveyance and analysis processes. Ideally, these conditions should be as close to the borehole in-situ environment as possible, or at least be kept within a sufficiently safe margin from certain thermodynamically critical values beyond which the formation fluid sample might be irreversibly altered.

One such critical formation fluid property is the bubble point pressure of crude oil (also referred to herein as the "bubble point"). If the borehole pressure is allowed to drop below the bubble point during oil production, gas bubbles will form in the porous rock reservoir dramatically decreasing the oil phase relative permeability. Accordingly, a reliable determination of the bubble point pressure is vital for complete characterization of a reservoir zone and its subsequent commercial exploitation. Further, knowledge of the bubble point is also useful in determining the composition of the hydrocarbon mixture in the reservoir.

One traditional method (referred to as the P-V technique) of measuring the bubble point is to bring a sample to the surface to be sent to a laboratory (called a PVT Laboratory). There, the sample is placed in a cylinder. The volume of the cylinder is then increased using a piston and the pressure is monitored. Using this method, the bubble point is the pressure at which a break (knee) appears in the pressure versus volume (P-V) curve.

However, the P-V technique has several disadvantages. One major drawback is that it is time consuming to bring a fluid sample to the surface, transfer it to the (possibly distant) laboratory, and await the results. Typically, a delay of several weeks occurs between the time of fluid sampling and the receipt of the laboratory report log. By the time the laboratory report is received, it may be too late to obtain additional samples. Further, because samples may be altered by pressure and/or temperature changes when they are brought to the surface and sample composition can change as a result of imperfect transfer from sampling bottle to transportation bottle and then to laboratory apparatus, the P-V technique may be unreliable. Further limitations of this technique are: (1) only a few samples (typically six or fewer) can be transported to the surface on each tool run; and (2) high pressure, toxic, and potentially explosive samples must be transported, handled, and disposed of, creating numerous potential health, safety and environmental problems.

Due to these problems, improved bubble point measurement techniques have been developed. In one such technique, bubble formation is observed in a cylinder by use of a sight glass. In this manner, bubbles are detected visually. Because the bubble point is associated with the attenuation of a light beam, more sophisticated methods measure the transmission of near infrared light.

Several additional methods have been proposed in which the bubble point pressure measurement can be made in-situ using a borehole tool. Existing formation sampling tools, such as the MDT by Schlumberger, employ a mechanically actuated expanding volume to control the draw-down pressure during fluid sampling and an optical analyzer to detect the first occurrence of gas bubbles. However, this measurement process can be time-consuming and inconsistent and has the attendant risk of losing the tool in the borehole.

More recently, cavitation has been identified as an ideal method for determining bubble point pressure in-situ using a borehole tool. As discussed in commonly owned U.S. Pat. No. 6,128,949 to Kleinberg (the '949 Patent), acoustic cavitation refers to the generation of low-pressure regions in a liquid, which induces the evolution of gas bubbles. It has been established that for a liquid near the bubble point (i.e., the point at which bubbles are thermodynamically stable but form slowly), modest localized pressure reductions, such as are induced by acoustic waves, can lead to efficient evolution of bubbles. The '949 Patent is incorporated herein by reference in its entirety.

Conventional ultrasonic transducers do not operate well in the 175° C. and 20,000 psi borehole environment. Typical commercially available high-power ultrasonic transducers, due to less robust design, fabrication and construction criteria, are intended for use at surface pressures and temperatures and have not been adapted for use to nucleate bubbles in borehole-like conditions. Accordingly, there exists a need for an ultrasonic transducer suitable for use in a borehole tool that is capable of withstanding the harsh borehole environment and that is capable of nucleating bubbles in static pressures above the bubble point. While some drilling environments may exceed these operating conditions, these parameters generally are considered a baseline for the design of an ideal device.

Further, it is desirable to use a tool that does not impact, or only minimally impacts, the existing flow operation of the fluid sampling mechanism. For example, it is preferred to use a design that does not require an enlargement of the flow cross-section in mid-stream. Furthermore, the ideal design should not require a large sampling volume that is filled and evacuated separately and repeatedly.

Accordingly, one object of the present invention is to provide a device that can efficiently and advantageously induce and detect bubble formation at a significant static pressure margin above the bubble point pressure.

One further object of the present invention is to provide a device that is operable at temperatures and pressures up to 175° C. and 20,000 psi.

A further object of the present invention is to provide a device whose design will integrate seamlessly into the flow-line structure of a host tool and is power-efficient.

Yet another object of the present invention is to provide an ultrasonic transducer/resonator suitable for use in the method of the '949 Patent.

And, yet another object of the present invention is to provide a borehole bubble point measuring apparatus that has no moving parts and, therefore, is not prone to failure in a "dirty" borehole environment.

SUMMARY OF THE INVENTION

The present invention discloses an apparatus useful for nucleating bubbles and allowing the determination of the bubble point pressure in a borehole environment. In one embodiment, an acoustic resonator device is disclosed having one or more coaxial layers forming a central conduit in fluid communication with a borehole formation fluid sampling means, wherein at least one of the coaxial layers is comprised of an electro-acoustic transducer material. While this device is preferably designed to be in fluid communication with a host tool to allow in-situ sampling and bubble point determination, it may be used in surface systems on samples under borehole like conditions. The device may be used in a tool using a captured volume sampling technique or a flow-line sampling technique (e.g. a portion of the fluid moving within a flow-line).

Also disclosed is an in-situ method of fluid analysis in the borehole of a well for determining phase characteristics of a formation fluid comprising the steps of: (a) withdrawing a formation fluid sample using a formation sampling tool equipped with an acoustic cavitation device having one or more coaxial layers forming a central conduit, wherein at least one of the one or more coaxial layers is comprised of an electro-acoustic transducer material; (b) activating the electro-acoustic transducer material thereby nucleating bubble formation in the sample; (c) detecting an onset of bubble formation within the central conduit; and (d) measuring pressure of fluid at the onset of bubble formation in accordance with step (c).

The present invention may be used to induce bubble nucleation in nearly any sample wherein the anticipated bubble point pressure is lower than the static sample pressure (for example tens to hundreds, and possibly even thousands, of psi difference). Most preferably, this device is suited to induce bubble nucleation under borehole-like conditions. In this embodiment of the present invention, a fluid sample is obtained, wherein the fluid sample has a static pressure higher than an expected bubble point pressure (in some cases possibly thousands of psi higher), using a sampling tool equipped with an acoustic cavitation device having one or more coaxial layers forming a central conduit, wherein at least one of the coaxial layers is comprised of an electro-acoustic transducer material. The electro-acoustic transducer material is activated to nucleate bubbles in the sample. Bubble formation may then be detected within the central conduit and the pressure of fluid measured at the onset of bubble formation.

Further features and applications of the present invention will become more readily apparent from the figures and detailed description that follows.

DETAILED DESCRIPTION

Figure 1:
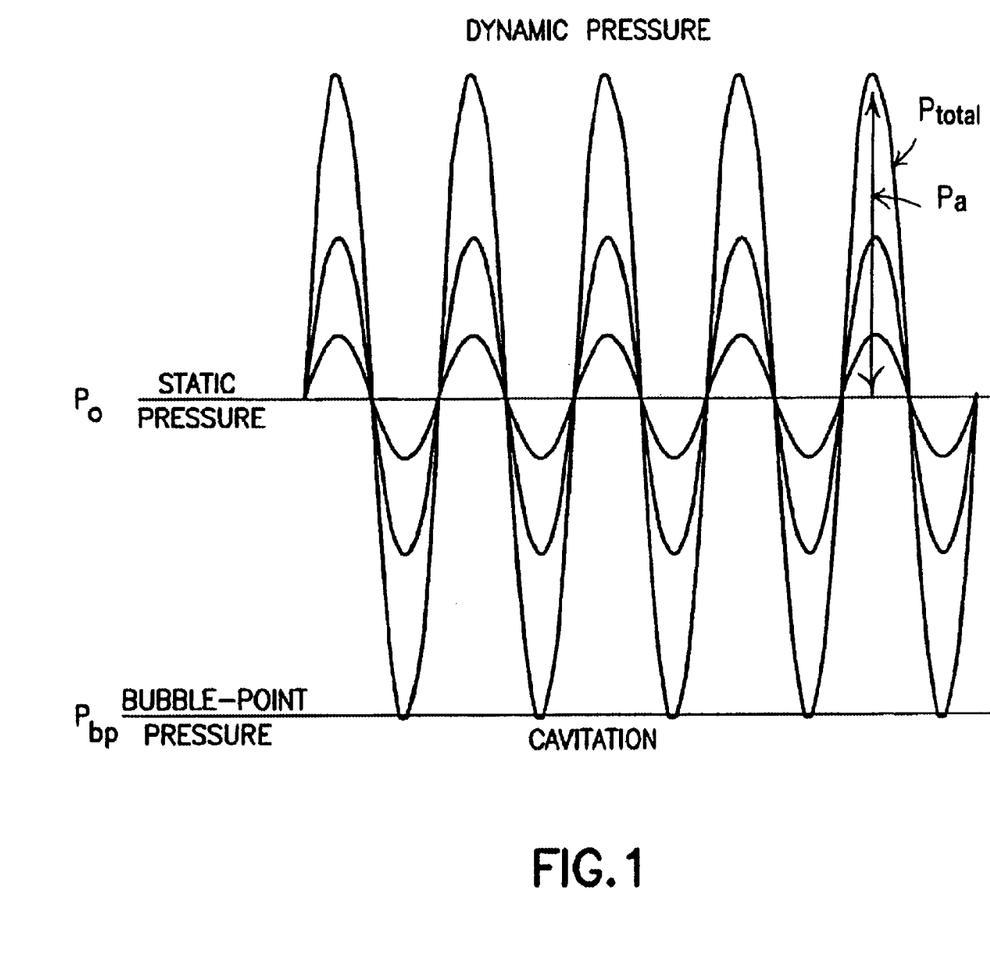
FIG. 1 is a graphical representation of the use of dynamic pressure fluctuation to induce bubble evolution in an extracted formation liquid sample under borehole conditions.

Bubble point pressure is defined thermodynamically as the pressure at which the most volatile component in a liquid starts coming out of solution. Acoustic cavitation refers to the generation by some active means of low-pressure regions in a liquid, thereby inducing the evolution of gas bubbles. Cavitation as a physical phenomenon is well studied. FIG. 1 illustrates the underlying concept. By way of example, consider an acoustic source immersed in a liquid at an ambient pressure of $p_o$ (the static pressure) in the liquid. If a source excites a sinusoidal pressure fluctuation of amplitude $p_a$ in the liquid, the total pressure in the liquid is simply the sum of the static pressure and the dynamic fluctuation:

$$p = p_o + p_a \sin \omega t$$

The minimum total pressure occurs at the rarefaction troughs of the sinusoidal waveform:

$$p_{min} = p_o - p_a$$

If the dynamic pressure amplitude $p_a$ is increased sufficiently such that the minimum total pressure is lower than the bubble point pressure $p_{bp}$, $$p_{min} < p_{bp}$$

bubbles will evolve. According to the theory of "rectified diffusion of gas," the newly formed gas phase does not go back in solution across the liquid/gas boundary as easily as it emerges from solution, even as the total pressure returns momentarily above the bubble point pressure. Thus, successive up and down swings of the dynamic pressure give rise to a net accumulation of gas bubbles. This illustration is a simple, first-order definition of acoustic cavitation. It also shows that bubbles may be induced while operating at a static pressure safely above the bubble point. Furthermore, with a known static (or operating) pressure and a good calibration of the dynamic pressure amplitude $p_a$ versus the input drive of the acoustic source, one can quantitatively determine the bubble point pressure by increasing the dynamic pressure amplitude while observing the onset of bubbles.

The present invention describes a device that may be used to induce acoustic cavitation in a formation liquid sample based on this bubble point theory that meets the operating design requirements described above. The design is based on the electromechanical resonance concept to maximize dynamic pressure output for a given electrical drive input and to minimize expenditure of real electrical power. The implementation takes into account the requisite borehole operating environment, the general flow operation of the formation fluid sampling process, and the ultimate manufacturability of a practical device. The device of the present invention is capable of inducing bubble formation in situations where the static (or operating pressure) of FIG. 1 is much higher than the bubble point pressure. In borehole environments, this method may be used to induce bubble nucleation where the bubble point pressure is lower than the static pressure. Accordingly, the device is capable of inducing dynamic pressures on a borehole fluid sample, thereby inducing bubble formation.

Figure 2:
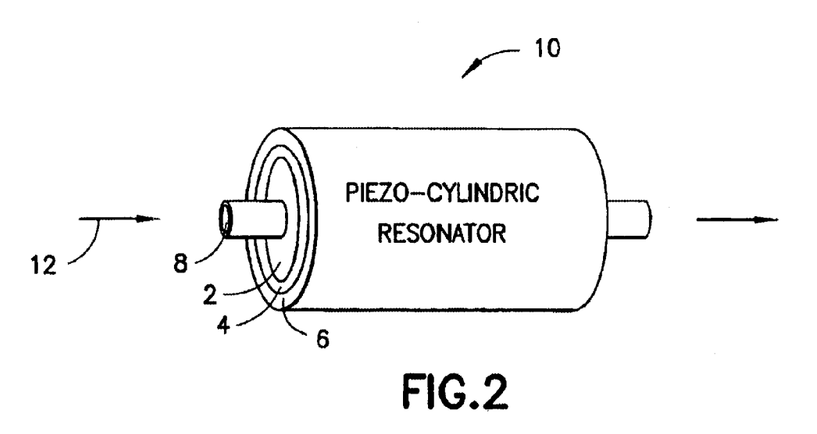
FIG. 2 is a schematic representation of a multi-layered coaxial resonator of the present invention.

FIG. 2 depicts a basic acoustic cavitation device of the present invention. The device 10 includes one or more coaxial layers 2, 4, 6 with a central conduit 8 that is in fluid communication with a sampling means 12. The sampling means may include a captured volume sampling device or a flow-line sampling device. For example, the device may be adapted to analyze captured volume samples obtained using the method and apparatus disclosed in commonly owned U.S. Pat. No. 4,951,749 to Carroll, entitled "Earth Formation Sampling and Testing Method and Apparatus with Improved Filter Means" or commonly owned U.S. Pat. No. 6,223,822 to Jones, entitled "Downhole Sampling Tool and Method." The device may also be adapted to analyze a sample within a flow-line using the method and apparatus disclosed in commonly owned U.S. Pat. No. 6,058,773 to Zimmerman et al., entitled "Apparatus and Method for Sampling Formation Fluids Above the Bubble Point in a Low Permeability, High Pressure Formation." One skilled in the art would recognize that other borehole sampling means may be suitably adapted. U.S. Pat. Nos. 4,951,749, 6,058,773, and 6,223,822 are incorporated by reference herein in their entireties.

The coaxial layers 2, 4, 6 form a fluid conduit 8 and do not interfere with the sampling means 12. The number of coaxial layers employed will depend on the number of additional functions to be performed by the device. Preferably, at least one of the layers is made of an electro-acoustic transducer material that converts electrical excitation into mechanical vibration and mechanical vibration into electricity. Preferably, the electro-acoustic transducer material is a piezo-electric material or a magnetostrictive material, most preferably it is lead zirconate titanate (PZT-8).

The coaxial layers 2, 4, 6 and the central conduit 8 form an electromechanical resonator. Electromechanical resonance generated by the device 10 is exploited to maximize the dynamic pressure amplitude inside the central conduit 8 for a given level of electrical drive for the primary purpose of inducing bubble evolution.

The overall diameter of the device will depend on the borehole size and tool string used as well as the desired operating frequency. The overall diameter may be between 15 mm (which generates a 100 kHz frequency) and 90 mm (which generates a 20 kHz frequency), most preferably 31 mm, and is sufficiently compact to fit inside the tool housing of a typical borehole tool. The ratio of overall length to diameter of the device 10 should be maximized. For practical applications, the ratio should be between about 1:1 and 20:1; most practical applications require about a 10:1 ratio. A large ratio ensures that the dominant vibration at resonance is radial with little axial motion, encouraging an efficient build-up of pressure in the fluid in the central conduit 8. Some axial motion is acceptable at the upstream and downstream ends of the device 10.

The nature of the axisymmetric design allows the acoustic field of this device 10 to focus along the symmetry axis (i.e., along the center line of the central conduit 8). A local maximum thus forms in the dynamic pressure field along this axial line. A long axisymmetric geometry (pseudo 1-D geometry) lends itself to a 1-D mathematical analysis. An exact 1-D model has been derived and implemented numerically to predict the electromechanical behavior of axisymmetric multi-layer electromechanical resonators with piezo-electric drive layers. This model will be discussed in more detail below.

Figure 3:
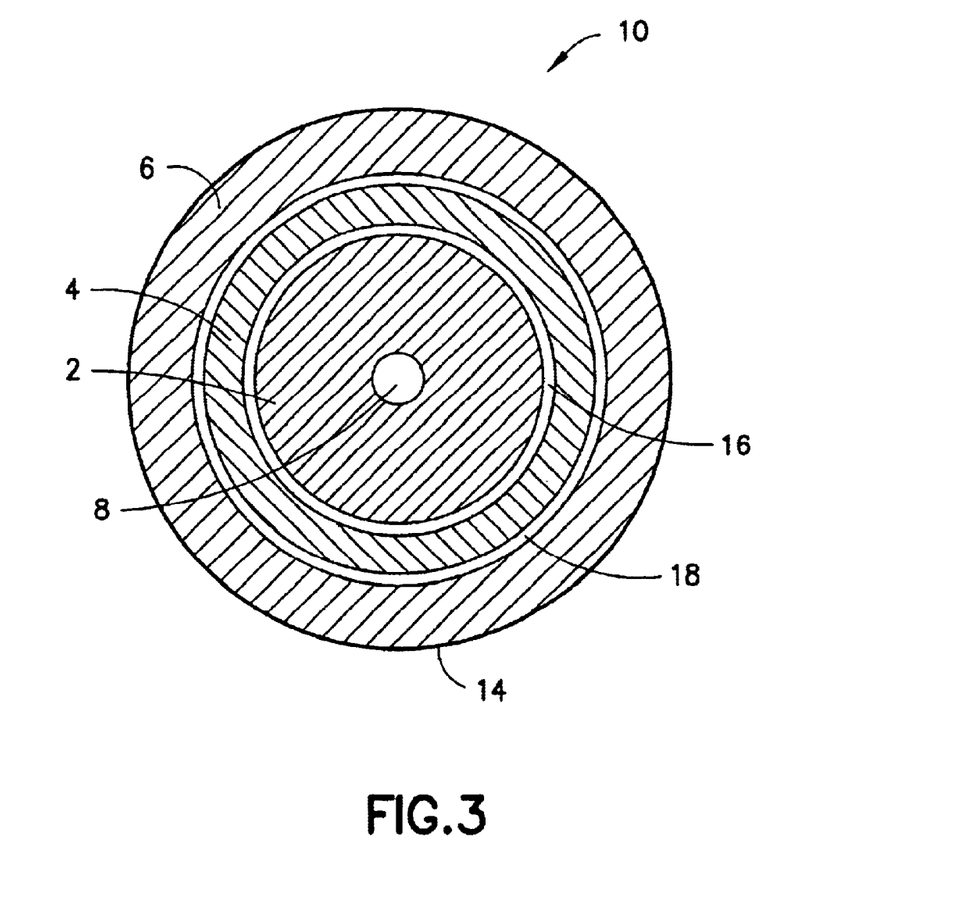
FIG. 3 is a cross section schematic of the multi-layered coaxial resonator of the present invention.

FIG. 3 shows a cross-sectional schematic of the device 10. The diameter of the central conduit 8 will depend on the overall diameter of the device. Most applications will require a conduit between about 0.75 and 10 mm in diameter, most practically about 5 mm. The diameter of the central fluid conduit 8 is similar to that of typical high-pressure flow-lines and can be incorporated smoothly into general flow plumbing. Accordingly, device 10 may share a sampling means with a host tool.

The inner layer 2 of the depicted embodiment will also depend upon the overall diameter of the device. Most practical applications will require a diameter between about 4 and 20 mm thick, most practically 6.5 mm. Preferably, the inner layer 2 is made of (or lined with) a substantially acoustically transparent or a low-acoustic loss material with a mass density and acoustic velocity substantially the same as the fluid under test. As one possible practical embodiment, the device tested herein had a PEEK lining. Further, the inner layer 2 may be comprised of individual sub-layers.

The middle layer 4 will also depend upon the overall diameter of the device. Most practical applications will require a diameter between about 2 and 6 mm thick, most practically 2.5 mm. The middle layer 4 is ideally an electro-acoustic transducer material, preferably, a piezo-electric material or a magnetostrictive material able to withstand borehole operating temperatures and pressures. Most preferably, it is comprised of lead zirconate titanate (PZT-8). Further, to enhance the electrical drive, the middle layer 4 may be comprised of individual sub-layers.

The outer layer 6 will depend on the overall diameter of the device. Most applications will require a diameter of between about 2 to 15 mm thick, most preferably 4 mm. This outer layer 6 or sleeve functions as a pressure containment means and should be strong enough to withstand full flow-line operating pressure which may reach up to 20,000 psi as well as borehole operating temperatures which may reach up to 175° C. Elevated temperatures and pressures are also referred to as borehole-like conditions. The outer layer 6 maybe made of one or more sub-layers and is preferably made of steel or similar strength material as it serves as the principal pressure containment housing.

In accordance with a resonator design, the cylindrical structure 10 should be as acoustically isolated as possible to minimize loss of resonant acoustic energy by radiation. The outer surface 14 of the outer layer 6 may be separated from the host tool by means of a gap, such as an air gap or a vacuum gap.

The piezo-electric layer 4, although strong under compression, is nonetheless a brittle material that may shatter when subject to tensile stress. Accordingly, it is typically not practical to assemble neighboring layers 2, 6 to the piezo-electric layer 4 using common interference fitting techniques. Even if the layers were force-fitted together without breakage during assembly, the piezo-electric layer 4 may still break during normal operations. Further, the layers 2, 4, 6 may not maintain tight acoustic coupling during operating conditions. As shown in FIG. 3, these manufacturing and operational issues may be avoided by using small gaps (approximately 75 μm thick) 16, 18 between the piezo-electric layer 4 and the adjacent inner layer 2 and outer layer 6. Accordingly, the layers 2, 4, 6 can therefore be assembled with relative ease due to the clearance gaps 16, 18 by design.

These two gaps should be filled with a pressurized non-corrosive hydraulic liquid, such as silicone oil or ethylene glycol to maintain good acoustic coupling among layers 2, 4, and 6. A preferred hydraulic liquid will have zero acoustic loss. Further, a sufficiently large static pressure, such as between 5,000 and 20,000 psi, preferably between 5,000 and 8,000 psi, most preferably 8,000 psi, applied to the hydraulic liquid ensures acoustic coupling between the piezo-electric layer 4 and the adjacent inner layer 2 and outer layer 6 throughout the entire operation envelope of the device. In addition, the static hydraulic pressure establishes static compressive biases in the piezo-electric layer 4 in both the radial and circumferential directions ensuring that layer 4 remains in compression during operation.

Physical connection to the flow plumbing lines at either end of the device 10 requires that the device be in physical contact with an external structure, such as the tool. While a perfect acoustic isolation is nearly impossible, the cross-sectional area of physical connection between the device and external structures should be minimized.

Figure 4:
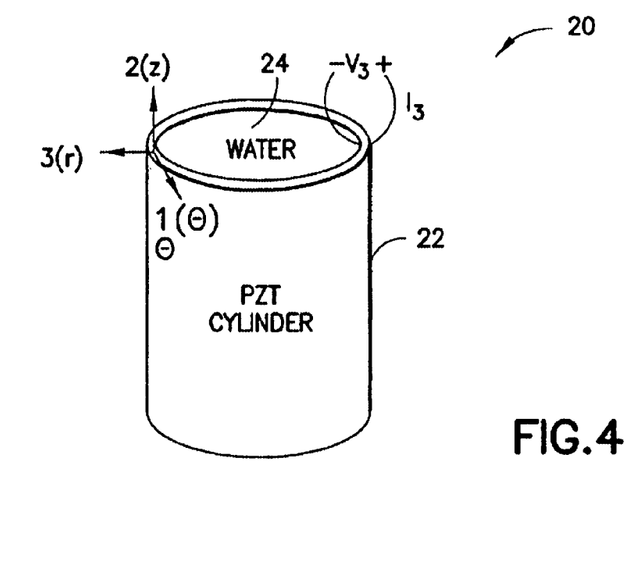
FIG. 4 is a schematic of a simple two-layered piezo-electrically driven resonator.

The device of the present invention may be implemented using multiple layers, i.e. N number of layers. For simplicity, the present invention will be described in terms of a two-layer example. FIG. 4 depicts a simplified resonator structure 20 used to describe the present invention. This simple structure includes a piezo-electric cylinder 22 filled with water 24. The piezo-electric cylinder 22 is radially poled and contains electrodes (not shown) on both the inner and the outer cylindrical surfaces so that a radial electric field may be applied across the thickness of the material. A multi-layer 1-D axisymmetric resonator computer model is used to identify and track the electromechanical resonance modes of the structure of the present invention. To explain the acoustic behavior of the simplified resonator of FIG. 4, the inner diameter of the piezo-electric layer 4 was changed while the thickness of this layer 4 was maintained at 2.5 mm.

Figure 5:
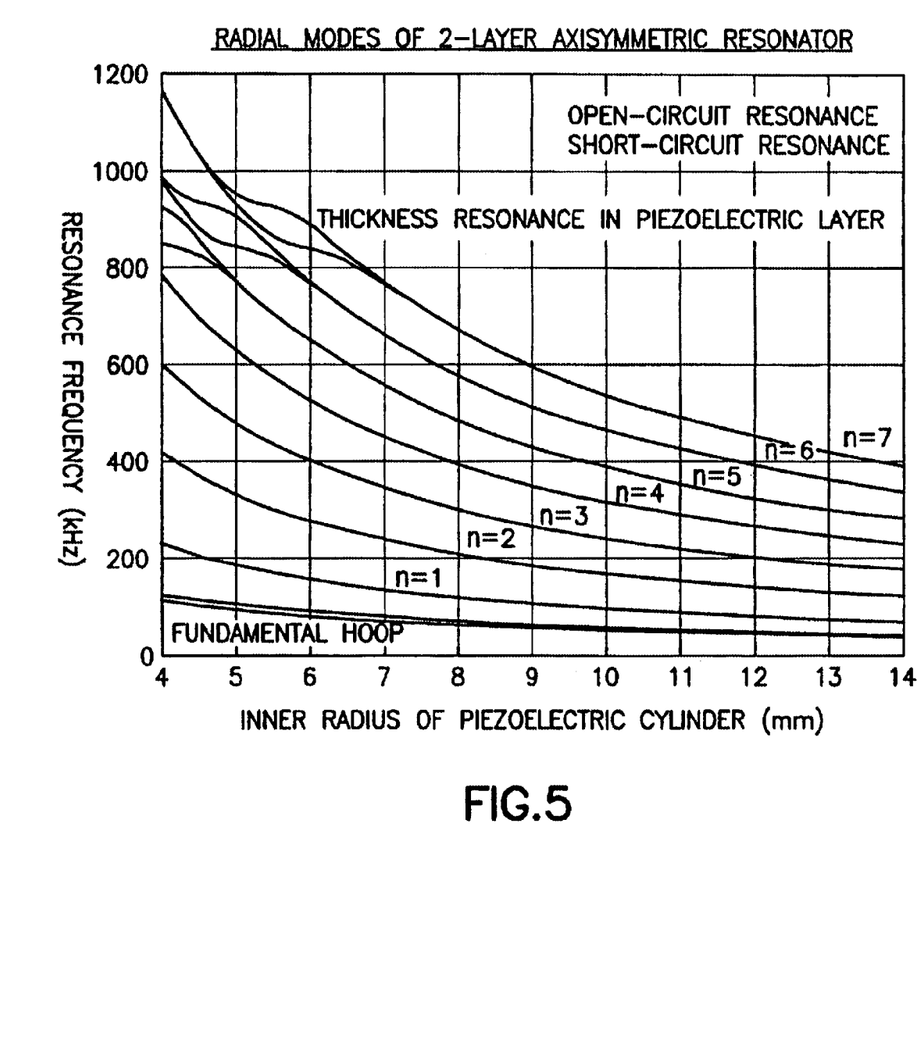
FIG. 5 is a graphical representation of electromechanical resonance modes of the simple two-layered piezo-electrically driven resonator of FIG. 4.

FIG. 5 summarizes the results of the simplified structure 20 in the form of dispersion curves. For a given diameter of the resonator, the lowest order resonance mode is the "hoop" mode and the higher order modes correspond essentially to the higher order radial modes in a water cylinder. The resonance frequency is inversely related to the size of the resonator and is not significantly affected by the wall thickness of the piezo-electric layer 22 of FIG. 4. However, at around 900 kHz, the thickness of the piezo-electric strongly disturbs the dispersion curves. Each resonance mode exhibits an open-circuit resonance (i.e. high electrical impedance) and a short-circuit resonance (i.e. high electrical admittance). The short-circuit resonance frequency, $f_{sc}$, is always lower than the corresponding open-circuit resonance frequency, $f_{oc}$. In general, as the separation between $f_{sc}$ and $f_{oc}$ increases, the electromechanical coupling in the resonator becomes stronger, more efficiently converting electrical drive into mechanical vibration. FIG. 5 clearly shows that the fundamental hoop mode gives much higher electromechanical coupling than the higher order modes with the exception of the cases where the thickness resonance of the piezo-electric layer 22 overlaps with the resonance modes of the water (at about 900 kHz).

Because ultrasonic cavitation is most efficiently induced at low acoustic frequencies (at less than about 100 kHz), and since the hoop mode provides the lowest frequency of operation for a given resonator size, it is preferable to use this mode as the primary resonance mode. Further, the hoop resonance frequency does not change drastically with the physical state (gas or liquid) of the fluid in the central conduit 8 as shown in FIG. 2. This benign attribute allows the associated drive electronics (not shown) to easily track the operating frequency of the device 10 within a reasonable range in the event of abrupt changes that may affect the fluid flow 8 during normal operation.

To achieve high conversion efficiency in the device 10, materials having low mechanical losses should be chosen for the coaxial layers 2, 4, 6. Further, the piezo-electric layer 4 should have low electrical loss. While loss characteristics of the formation fluid in the central conduit 8 cannot be readily controlled, layers 2, 4, 6 should be chosen with the highest mechanical and electrical quality factors (Q) feasible, such as steel and PZT-8. PZT-8 is a preferred piezoelectric material for layer 4 as it has a large piezo-electric coupling coefficient, a large dielectric constant and a low dielectric loss tangent. A low loss system reduces the real electrical power requirements of the drive electronics and minimizes bulk heating of the device and, in turn, the formation liquid sample, thereby preserving the accuracy of the bubble point measurements.

Figure 6A:
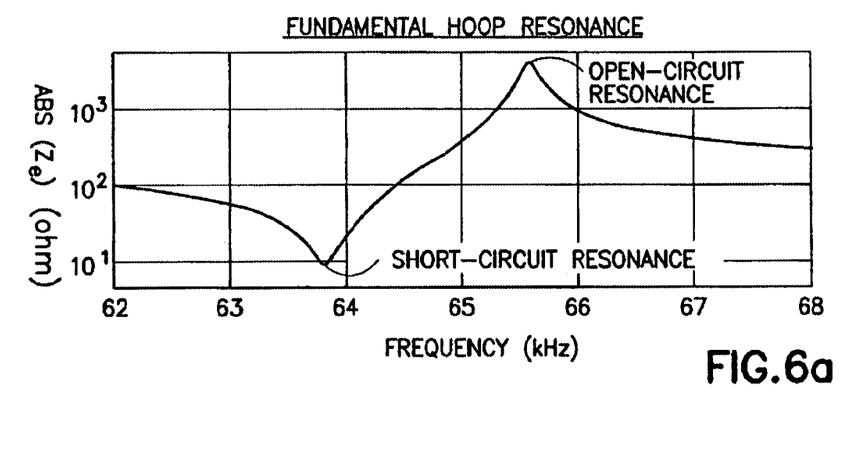
FIGS. 6a and 6b are graphical representations of the electrical impedance of the cylindrical multi-layered resonator design shown in FIG. 3 in the vicinity of the fundamental hoop resonance.
Figure 6B:
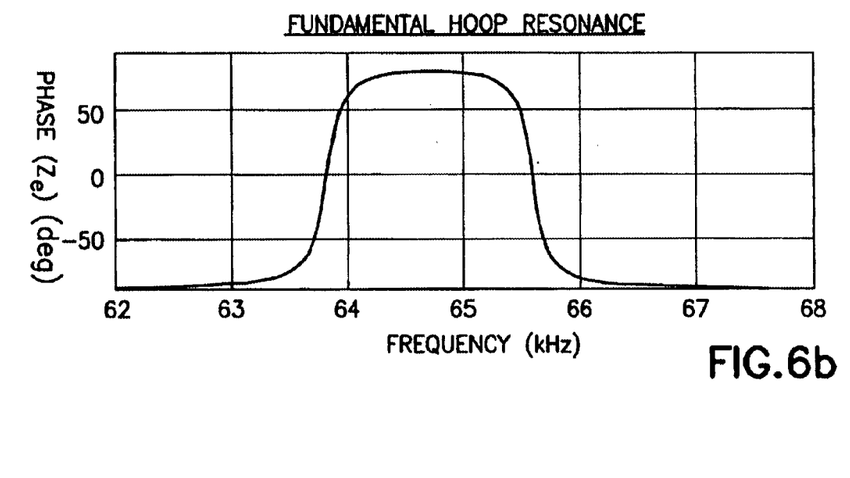

FIGS. 6a and 6b show the theoretical electrical impedance of the device 10 of the present invention. For modeling purposes, the central conduit 8 was filled with water and the axial length of the device 10 was set at 75 mm (about 2.5 times the outer diameter). The results show that the fundamental hoop mode of the device has an open-circuit resonance at 65.50 kHz and short-circuit resonance at 63.83 kHz. To attain maximum electromechanical efficiency, the device should be operated at one of the two resonance frequencies depending on whether the electrical driver approximates a current source or a voltage source. At the short-circuit resonance, the device 10 presents an impedance of 9.8-j0.5 ohms. The real part of the impedance reflects loss due to the finite material Q's. Real electrical power is supplied to the resonator to sustain mechanical vibration, but it is ultimately lost to thermal heating. The imaginary part of the impedance is indicative of a series capacitive load that generally can be compensated for by inductive tuning.

Figure 7A:
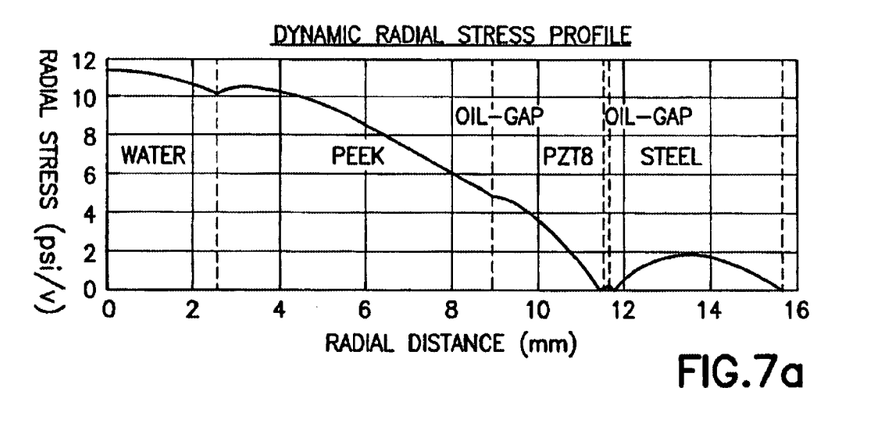
FIGS. 7a and 7b are graphical representations of the dynamic stress profiles of the cylindrical multi-layered resonator design shown in FIG. 3 at the short-circuit fundamental hoop resonance.
Figure 7B:
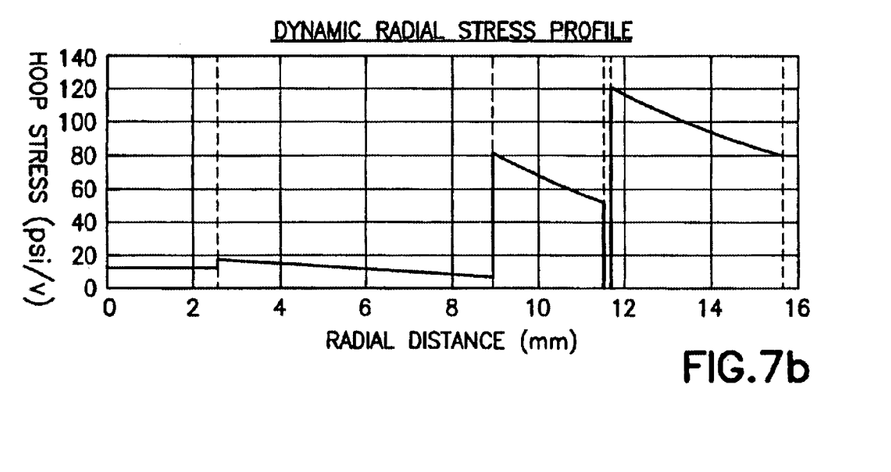

The radial and hoop dynamic stress profiles can be computed using the N-layer 1-D model discussed above. FIGS. 7a and 7b show the dynamic radial and hoop stress profiles inside the resonator device 20 at the short circuit resonance. The radial stress profile exhibits a very desirable global maximum in the center of the central conduit 24.

No unduly large build-up of radial stress occurs elsewhere in the resonator structure. The pressure-to-voltage conversion ratio peaks at about 11 psi/volt along the axis of the central conduit 24. This conversion ratio can be characterized precisely through numerical modeling and experiments. Combined with an accurate measurement of the static ambient pressure and a reliable detection of bubble evolution, quantitative determination can be made of the bubble point pressure of the extracted formation liquid.

The dynamic hoop stress profile shows that the hoop stress in the piezo-electric layer 4 can be more than an order of magnitude higher than the radial stress, and is therefore the dominant failure mode during high-amplitude operation. The static pressure applied to the hydraulic liquid 16, 18 to either side of the piezo-electric layer 4 has to be sufficiently high to compensate for the largest possible dynamic hoop stress throughout the operating envelope of the device 10.

Because bubbles may not readily form at the thermodynamic bubble point, especially if the bulk of the liquid sample is stagnant, some external stimulus (such as physical agitation) could trigger a violent evolution of bubbles. This phenomenon is referred to as supersaturation and may result in a significant under-estimation of the bubble point pressure.

In a PVT laboratory, typically the sample is stirred to enhance bubble evolution and improve the likelihood that the true thermodynamic bubble point pressure is identified. The present invention simulates this stirring without the need for moving parts. The large amplitude dynamic pressure field that occurs at resonance in the liquid conduit 8 generates a finite radiation pressure field that encourages bulk movement of the liquid sample, a phenomenon called acoustic streaming.

The borehole is a dirty environment and the extracted formation fluids are complex in that they may contain sediments and/or sticky solids that could precipitate from the liquid phase. Clogging of flow-lines in a borehole sampling tool is a perennial problem. Because the device 10 does not use moving parts, failure due to clogging will typically not be an issue. In fact, large amplitude vibrations at the wall of the fluid conduit during operation of the resonator device 10 tend to dislodge deposits, thus providing a self-cleaning function that sustains flow continuity.

Figure 8A:
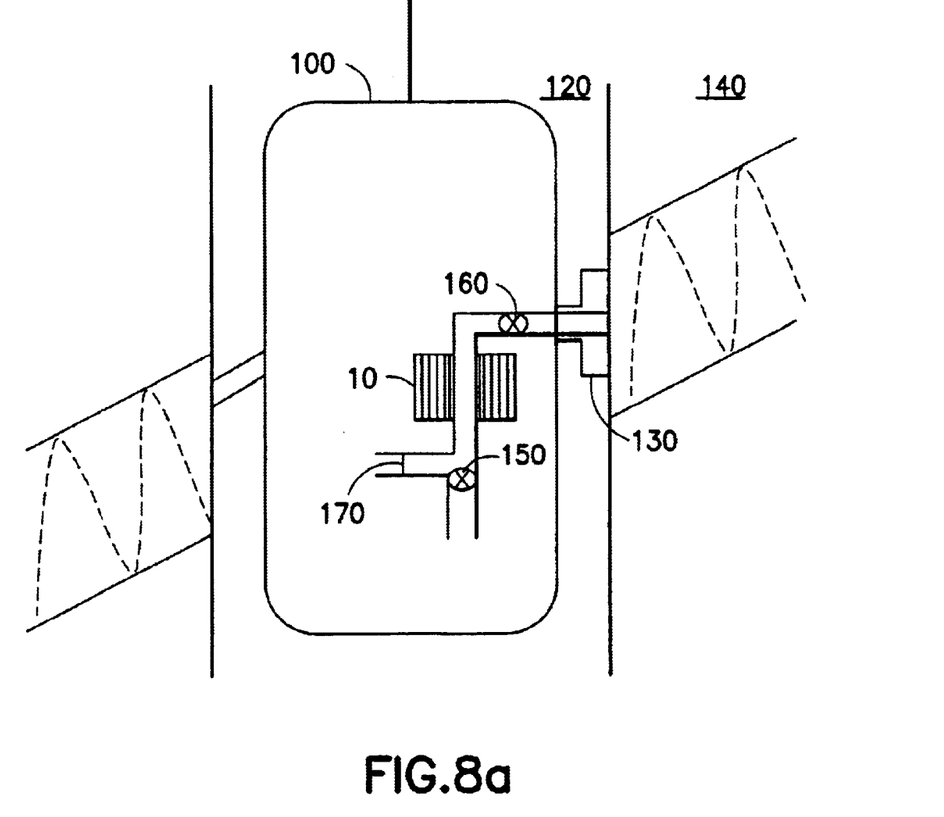
FIGS. 8a and b are schematics of sampling devices useful in hosting the device of the present invention.
Figure 8B:
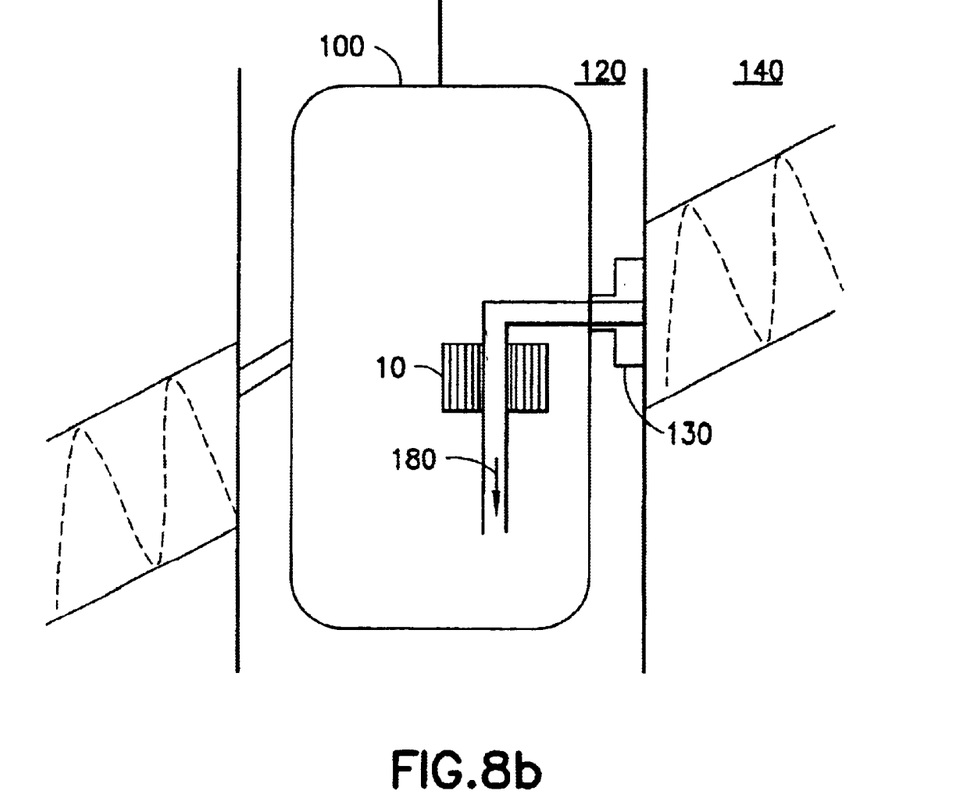

As indicated above, the present invention may be implemented in a tool string having a captured volume sampling means or a flowing sample means. FIGS. 8a and b are schematic diagrams of a borehole apparatus useful in the present invention. In this non-limiting embodiment, the tool 100 equipped with the device of the present invention 10 is suspended in the borehole 120. The sampling means 130 is used to obtain a formation fluid sample from the formation 140. FIG. 8a shows one embodiment wherein the sampling means obtained a captured or fixed volume sample. Valves 150 and 160 isolate a portion of the formation fluid. The sample is depressurized using the piston 170. Bubbles are cavitated and/or detected using the transducer 10. FIG. 8b shows another embodiment wherein the transducer 10 cavitates and/or detects bubbles in a sample flowing 180 through the transducer 10. One skilled in the art would recognize that other tools may be suitably adapted.

Furthermore, the present invention is not limited to borehole applications. It may be suitably employed in surface apparatus, PVT Laboratory settings and other bubble cavitation and identification applications.

While the invention has been described herein with reference to certain examples and embodiments, it will be evident that various modifications and changes may be made to the embodiments described above without departing from the scope and spirit of the invention as set forth in the claims.

What is claimed is:

1. An acoustic device for use in a borehole environment to cavitate bubbles in a formation fluid to determine formation fluid characteristics comprised of: one or more coaxial layers forming a central conduit in fluid communication with a borehole formation fluid sampling means, wherein at least one of said one or more coaxial layers is comprised of an electro-acoustic transducer material and configured to cavitate bubbles in said formation fluid, and wherein said device is adapted for connection to a host tool such that said host tool and said device share said sampling means.

2. The device of claim 1, wherein said sampling means is a captured volume sampling device.

3. The device of claim 1, wherein said sampling means is a flow-line sampling device.

4. The device of claim 1, wherein said electro-acoustic transducer material is a piezo-electric material.

5. The device of claim 1, wherein said electro-acoustic transducer material is a magnetostrictive material.

6. The device of claim 1, wherein said layer comprised of electro-acoustic transducer layer is further comprised of one or more sub-layers.

7. The device of claim 1, wherein said one or more coaxial layers have a length to diameter ratio greater than 1:1.

8. The device of claim 7, wherein said ratio is between 1:1 and 20:1.

9. The device of claim 1, wherein said one or more coaxial layers are acoustically isolated relative to external structures.

10. The device of claim 1, further comprising an inner layer positioned to the inside of said electro-acoustic transducer layer and an outer layer positioned to the outside of said electro-acoustic transducer layer.

11. The device of claim 10, wherein said outer layer is comprised of one or more sub-layers.

12. The device of claim 10, wherein said inner layer is comprised of one or more sub-layers.

13. The device of claim 10, wherein said inner and outer layers are comprised of materials having low mechanical losses.

14. The device of claim 10, wherein said outer layer is comprised of steel.

15. The device of claim 10, wherein said inner layer is comprised of a substantially acoustically transparent material.

16. The device of claim 10, wherein said inner layer is comprised of a low acoustic loss material having a mass density and an acoustic velocity substantially similar to a sample under test.

17. The device of claim 1, wherein the cross-sectional area contact between said one or more coaxial layers at each end of said device and any external structures is minimized.

18. The device of claim 1, wherein said layer is comprised of an electro-acoustic transducer material is subject to radial and circumferential compression.

19. The device of claim 1, wherein said central conduit has a lining made of a substantially acoustically transparent material.

20. The device of claim 1, wherein said central conduit has a lining made of a low acoustic loss material having a mass density and an acoustic velocity substantially similar to a sample under test.

21. An acoustic device for use in a borehole environment to cavitate bubbles in a formation fluid to determine formation fluid characteristics comprised of: one or more coaxial layers forming a central conduit in fluid communication with a borehole formation fluid sampling means, wherein at least one of said one or more coaxial layers is comprised of an electro-acoustic transducer material and configured to cavitate bubbles in said formation fluid, and wherein said device has an inner layer positioned to the inside of said electro-acoustic transducer layer and an outer layer positioned to the outside of said electro-acoustic transducer layer, a first hydraulic gap positioned between said layer comprised of electro-acoustic transducer material and said inner layer, and a second hydraulic gap positioned between said layer comprised of electro-acoustic transducer material and said outer layer.

22. The device of claim 21, wherein said first and second hydraulic gaps are subject to a static pressure.

23. The device of claim 22, wherein said static pressure is equal to between about 5,000 and 20,000 psi.

24. An acoustic device for use in a borehole environment to cavitate bubbles in a formation fluid to determine formation fluid characteristics comprised of: one or more coaxial layers forming a central conduit in fluid communication with a borehole formation fluid sampling means, wherein at least one of said one or more coaxial layers is comorised of an electro-acoustic transducer material and configured to cavitate bubbles in said formation fluid, wherein said device has an inner layer positioned to the inside of said electro-acoustic transducer layer and an outer layer positioned to the outside of said electra-acoustic transducer layer; wherein a gap is positioned between the outer layer and a host tool.

25. The device of claim 24, wherein said gap is comprised of air.

26. The device of claim 24, wherein said gap is a vacuum gap.

27. An in-situ method of fluid analysis in the borehole of a well for determining phase characteristics of a formation fluid comprising the steps of:
   a. withdrawing a formation fluid sample using a formation sampling tool equipped with an acoustic cavitation device having one or more coaxial layers forming a central conduit, wherein at least one of said one or more coaxial layers is comprised of an electro-acoustic transducer material;
   b. activating said electro-acoustic transducer material thereby nucleating bubble formation in said sample;
   c. detecting an onset of bubble formation within said central conduit; and
   d. measuring pressure of fluid at the onset of bubble formation in accordance with step (c).

28. The method of claim 27, wherein said sample volume is a captured volume sample.

29. The method of claim 27, wherein said sample volume is a portion of said formation fluid moving within a flowline.

30. An apparatus for determining a phase change in a sample of formation fluid having high temperature and pressure comprised of: a host tool having a formation fluid sampling means in fluid communication with an acoustic cavitation device having one or more coaxial layers forming a central conduit, wherein at least one of said one or more coaxial layers is comprised of a piezo-electric material, wherein said acoustic cavitation device has a length to diameter ratio equal to at least 1:1, and wherein an inner layer positioned to the inside of said electro-acoustic transducer layer and an outer layer positioned to the outside of said electro-acoustic transducer layer.

31. The device of claim 30, further comprised of:
   a. a first hydraulic gap positioned between said layer comprised of electro-acoustic transducer material and said inner layer; and
   b. a second hydraulic gap positioned between said layer comprised of electro-acoustic transducer material and said outer layer.

32. The device of claim 30, wherein said inner layer is comprised of one or sub-layers.

33. The device of claim 30, wherein said electro-acoustic transducer layer is comprised of one or more sub-layers.

34. An acoustic device to induce bubble nucleation in a formation fluid to determine formation fluid characteristics comprised of: one or more coaxial layers forming a central conduit in fluid communication with a fluid sampling means, wherein at least one of said one or more coaxial layers is comprised of an electro-acoustic transducer material, wherein said sample is subject to borehole-like conditions, and configured to cavitate bubbles in said formation fluid, wherein said device is adapted for connection to a host tool.

* * * * *